(12) United States Patent
Redoña et al.

(10) Patent No.: US 12,137,654 B2
(45) Date of Patent: Nov. 12, 2024

(54) RICE CULTIVAR CLHA02

(71) Applicant: Mississippi State University, Mississippi State, MS (US)

(72) Inventors: Edilberto D. Redoña, Greenville, MS (US); Timothy W. Walker, Hernando, MS (US); Dwight G. Kanter, Clinton, MS (US)

(73) Assignee: Mississippi State University, Mississippi State, MS (US)

( * ) Notice: Subject to any disclaimer, the term of this patent is extended or adjusted under 35 U.S.C. 154(b) by 280 days.

(21) Appl. No.: 17/970,403

(22) Filed: Oct. 20, 2022

(65) Prior Publication Data

US 2023/0217878 A1 Jul. 13, 2023

Related U.S. Application Data

(60) Provisional application No. 63/298,533, filed on Jan. 11, 2022.

(51) Int. Cl.
*A01H 5/10* (2018.01)
*A01H 6/46* (2018.01)

(52) U.S. Cl.
CPC .............. *A01H 6/4636* (2018.05); *A01H 5/10* (2013.01)

(58) Field of Classification Search
None
See application file for complete search history.

(56) References Cited

U.S. PATENT DOCUMENTS 8,440,892 B2 * 5/2013 Moldenhauer ........... A01H 5/10
800/320.2

OTHER PUBLICATIONS

PVP201400523, Mississippi State University, 2014, retrieved from https://apps.ams.usda.gov/cms/adobeimages/201400523.pdf (Year: 2014).*
PVP200800366, Louisiana State University Agriculture Center. 2008. retrieved from https://apps.ams.usda.gov/cms/adobeimages/200800366.pdf (Year: 2008).*
Blanche SB, X Sha, DL Harrell, DE Groth, KF Bearb, LM White, SD Linscombe. 2011. Registration of 'CL 151' Rice. J. Plant Registration 5:177-180.
Bollich, CN, CW Magill, AB Livore, HH Hung, BD Webb, MA Marchetti. 1993. Registration of 'Rosemont' rice. Crop Sci. 33:877.
Bollich, CN, BD Webb, MA Marchetti, JE Scott. 1980. Registration of 'Newrex' rice 1 (Reg. No. 54). Crop Sci. 20:286-287.
Johnston, TH, BR Wells, MA Marchetti, FN Lee, SE Henry. 1979. Registration of 'Mars' rice (Reg. No. 49). Crop Sci. 19:743-744.
Kuenzel, KA, TH Johnston, FN Lee, BR Wells, SE Henry, RH Dilday. 1986. Registration of 'Tebonnet' rice. Crop Sci. 25:1126-1127.

* cited by examiner

*Primary Examiner* — Weihua Fan
(74) *Attorney, Agent, or Firm* — Quarles & Brady, LLP

(57) ABSTRACT

A rice cultivar designated CLHA02 is disclosed herein. The present invention provides seeds, plants, and plant parts derived from rice cultivar CLHA02. Further, it provides methods for producing a rice plant by crossing CLHA02 with itself or another rice variety and methods for combating undesired vegetation by contacting the disclosed rice seeds with an acetohydroxyacid synthase (AHAS)-inhibiting herbicide. The invention also encompasses any rice seeds, plants, and plant parts produced by the methods disclosed herein, including those in which additional traits have been transferred into CLHA02 through the introduction of a transgene or by breeding CLHA02 with another rice cultivar.

37 Claims, 1 Drawing Sheet

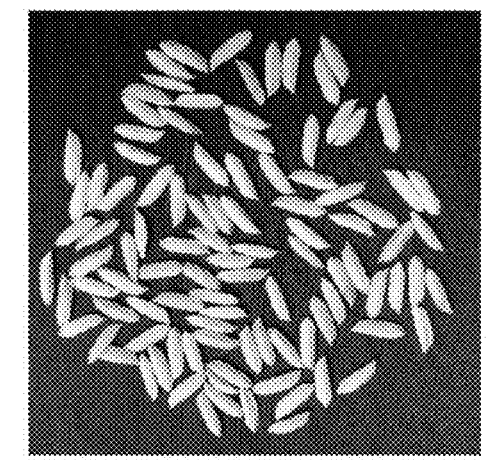
B.
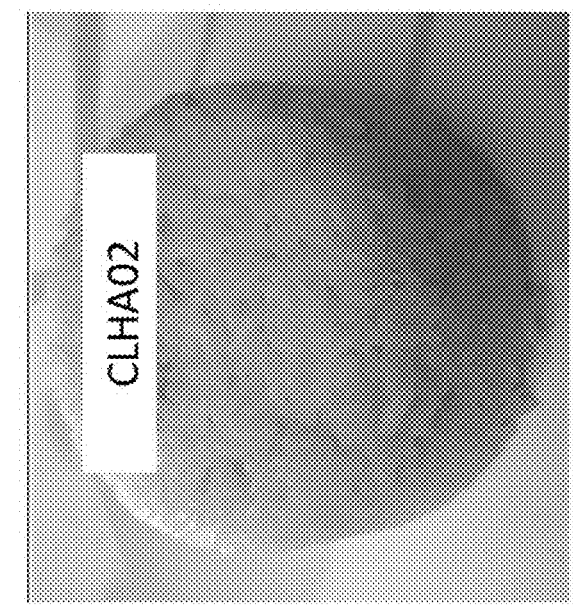
D.
A.
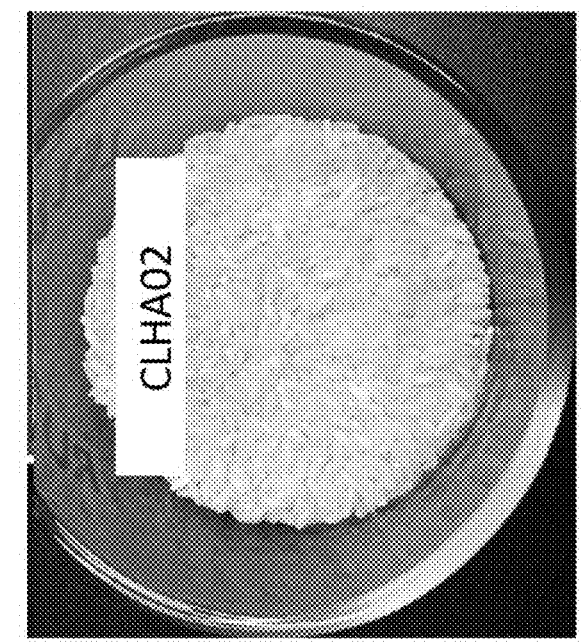
C.

RICE CULTIVAR CLHA02

CROSS-REFERENCE TO RELATED APPLICATIONS

This application claims priority to U.S. Provisional Application No. 63/298,533 filed on Jan. 11, 2022, the contents of which are incorporated by reference in their entireties.

STATEMENT REGARDING FEDERALLY SPONSORED RESEARCH

NR

BACKGROUND

The present invention relates to a new and distinctive rice cultivar, designated 'CLHA02.' Rice is an ancient agricultural crop and is today one of the principal food crops of the world. There are two cultivated species of rice: Oryza sativa L., the Asian rice, and O. glaberrima Steud., the African rice. O. sativa L. constitutes virtually all the world's cultivated rice and is the species grown in the United States. Three major rice producing regions exist in the United States: the Mississippi Delta (Arkansas, Mississippi, northeast Louisiana, southeast Missouri), the Gulf Coast (southwest Louisiana, southeast Texas), and the Central Valleys of California.

Rice is a semi-aquatic crop that benefits from flooded soil conditions during part or all of the growing season. In the United States, rice is grown on flooded soils to optimize grain yields. Heavy clay soils or silt loam soils with hard pan layers about 30 cm below the surface are preferred rice-producing soils because they minimize water losses from soil percolation.

Rice production in the United States can be broadly categorized as either dry-seeded or water-seeded. In the dry-seeded system, rice is sown into a well-prepared seed bed with a grain drill or by broadcasting the seed and incorporating it with a disk or harrow. Moisture for seed germination is provided by irrigation or rainfall. Alternatively, the seed may be broadcast by airplane into a flooded field, which is promptly drained following seeding. With the dry-seeded system, when the plants have reached a sufficient size (i.e., the four- to five-leaf stage), a shallow permanent flood of water, 5 to 16 cm deep, is applied to the field for the remainder of the crop season. In the water-seeded system, rice seed is soaked for 12 to 36 hours to initiate germination, and the seed is broadcast by airplane into a flooded field. The seedlings emerge through a shallow flood, or the water may be drained from the field for a short period of time to enhance seedling establishment. A shallow flood is maintained until the rice approaches maturity. For both the dry-seeded and water-seeded production systems, the fields are drained when the crop is mature, and the rice is harvested 2 to 3 weeks later with large combines. In rice breeding programs, breeders typically employ the production systems that are predominant in their region. Thus, a drill-seeded breeding nursery is typically used by breeders in a region where rice is drill-seeded, and a water-seeded nursery is typically used in regions where rice is water-seeded.

In the United States, rice is classified into three primary market types by grain size, shape, and chemical composition of the endosperm: long-grain, medium-grain, and short-grain. Typical U.S. long-grain cultivars cook dry and fluffy when steamed or boiled, whereas medium and short-grain cultivars cook moist and sticky. Traditionally, in the southern states, long-grain cultivars have been grown and generally receive higher market prices.

Rice, Oryza sativa L., is an important and valuable field crop. A continuing goal of plant breeders is to produce stable, high yielding rice cultivars that are agronomically sound. To accomplish this goal, rice plants with traits that result in superior cultivars must be developed.

SUMMARY

The present invention provides a novel rice cultivar designated CLHA02. The invention encompasses the seeds, plants, and plant parts of rice cultivar CLHA02, as well as plants with all of the physiological and morphological characteristics of CLHA02.

In another aspect, the present invention provides methods for controlling weeds in the vicinity of a rice plant of rice cultivar CLHA02 using an acetohydroxyacid synthase (AHAS)-inhibiting herbicide. In some embodiments, seeds of rice cultivar CLHA02 are treated with an AHAS-inhibiting herbicide. In other embodiments, the herbicide is applied post-emergence.

This invention also provides methods for producing a rice plant by planting a plurality of seeds or by crossing rice CLHA02 with itself or another rice line. Any plant breeding methods using rice cultivar CLHA02 are part of this invention, including selfing, backcrosses, hybrid production, and crosses to populations. All plants and seeds produced using rice cultivar CLHA02 as a parent are within the scope of this invention, including gene-converted plants of CLHA02. Methods for introducing a gene into CLHA02, either through traditional breeding, transformation or gene editing, are also provided herein.

In still another aspect, the present invention provides regenerable cells for use in tissue culture of rice plant CLHA02, as well as rice plants regenerated from these tissue cultures.

BRIEF DESCRIPTION OF THE DRAWINGS

FIG. 1 shows panicles (A), rough rice (B), milled rice (C), and cooked rice (D) of rice cultivar CLHA02.

DEFINITIONS

To provide a clear and consistent understanding of the specification and claims, the following definitions are provided:

Allele. One of two or more alternative forms of a gene, all of which relate to a single trait or characteristic.

Apparent amylose content. The amount of starch in the endosperm of milled rice that is amylose, provided in g/kg herein. Amylose content varies depending on the growth environment of the rice. It is an important grain characteristic used to describe cooking behavior.

Backcrossing. A process in which a breeder repeatedly crosses hybrid progeny back to a parental line. For example, a first generation ($F_1$) hybrid may be crossed with one of the parental lines used to produce the $F_1$ hybrids.

Breeding. The genetic manipulation of living organisms.

Cell. A cell is the basic structural unit of all organisms. As used herein, this term includes isolated cells, cells grown in tissue culture, and cells that are part of a plant or plant part.

Cultivar. Used interchangeably with "variety." Refers to plants with the characteristics of a particular genotype or combination of genotypes. Plants of a particular cultivar are distinguished from any other plant grouping by at least one characteristic.

Days to 50% heading. The average number of days from emergence to the day when 50% of all panicles are exerted at least partially through the leaf sheath. A measure of maturity.

Embryo. The plant embryo is the part of a seed or bud that contains the earliest forms of the new plant's roots, stem, and leaves.

Essentially all of the physiological and morphological characteristics. A plant having "essentially all the physiological and morphological characteristics" of the cultivar exhibits the characteristics of the cultivar with the exception of any characteristics derived from a converted gene, i.e., a gene that was transferred into the cultivar via backcrossing or genetic engineering.

$F_\#$. Denotes a filial generation, wherein the # is the generation number. For example, $F_1$ is the first filial generation.

Gene. Refers to a unit of inheritance corresponding to a distinct DNA sequence that forms part of a chromosome. A gene may encode a polypeptide or a functional nucleic acid molecule.

Gene-converted. Describes a plant wherein essentially all of the desired morphological and physiological characteristics of a parental cultivar are maintained with the exception of a single trait that was transferred into the cultivar via backcrossing or genetic engineering.

Genotype. Refers to the genetic constitution of a cell or organism.

Grain yield. Measured in pounds per acre at 12.0% moisture content. The grain yield of rice is determined by the number of panicles per unit area, the number of fertile florets per panicle, and the grain weight per floret.

Haploid. A cell or organism having a single set of unpaired chromosomes.

Harvest moisture. The percent moisture content of the grain when harvested.

Head rice. Kernels of milled rice in which greater than ¾ of the kernel is unbroken.

Herbicide resistant. Describes a plant that is tolerant or resistant to an herbicide at a level that would normally kill or inhibit the growth of a normal or wild-type rice plant.

Hybrid. Refers to the progeny of genetically dissimilar plant parents or to stock produced by controlled cross-pollination, as opposed to a non-hybrid seed produced by natural pollination.

Kernel length. Length of a rice grain, measured in millimeters.

Kernel width. Width of a rice grain, measured in millimeters.

Length/width (L/W) ratio. Determined by dividing the average length by the average width.

Lodging. The percentage of plant stems that are leaning or have fallen to the ground before harvest. Lodging is determined by visual scoring, in which crops are rated from 0% (all plants standing) to 100% (all plant lying flat on the soil surface). Lodged plants are difficult to harvest and reduce yield and grain quality. Lodging resistance is also called "straw strength".

Milling yield. The total amount of rice kernels (including both whole and broken kernels) recovered after milling (i.e., removal of hulls, bran, and germ). In contrast, "head rice yield" is the amount of whole kernels recovered after milling. Both values are expressed as a weight percentage of the original paddy or rough rice sample that was milled.

Milling quality is often presented as a ratio of head rice yield to total rice yield. For example, for a sample of 100 grams of rough rice, a milling yield of 65:70 indicates that 65 grams of head rice and 70 grams of total milled rice were produced.

Pedigree. Refers to the lineage or genealogical descent of a plant.

Plant. As used herein, the term "plant" includes plant cells, plant protoplasts, and plant cell tissue cultures from which rice plants can be regenerated; plant calli, plant clumps and plant cells that are intact in plants; and plant parts.

Plant height. Measured in centimeters from the soil surface to the tip of the extended panicle at harvest.

Plant parts. Includes, without limitation, protoplasts, leaves, stems, roots, root tips, anthers, pistils, seeds, grains, embryos, pollen, ovules, cotyledons, hypocotyls, pods, flowers, shoots, tissues, petioles, cells, and meristematic cells.

Progeny. Includes an $F_1$ rice plant produced from the cross of two rice plants, as well as plants produced from subsequent generational crosses (e.g., $F_2$, $F_3$, $F_4$, $F_5$, $F_6$, $F_7$, $F_8$, $F_9$, and $F_{10}$) with the recurrent parental line.

Regeneration. Refers to the development of a plant from tissue culture.

Seeds. Includes seeds and plant propagules of all kinds including, but not limited to, true seeds, seed pieces, suckers, corms, bulbs, fruit, tubers, grains, cuttings, cut shoots, and the like.

However, in preferred embodiments, this term refers to true seeds.

Trait. Refers to an observable and/or measurable characteristic of an organism. For example, the present invention describes plants that have a trait that make them resistant to acetohydroxyacid synthase (AHAS) inhibiting herbicides.

Transgenic. Describes an organism or cell that contains genetic material that has been artificially introduced.

Wild-type. Used to refer to a gene that is common throughout a population and is, thus, arbitrarily designated the "normal" or "wild-type" form of the gene.

DETAILED DESCRIPTION

The present disclosure provides a novel rice cultivar designated CLHA02. The disclosure encompasses both the seeds of this cultivar and plants grown from these seeds. The disclosure further encompasses any rice plant having all of, or essentially all of, the physiological and morphological characteristics rice cultivar CLHA02.

Development and Characterization of Rice Cultivar CLHA02:

Rice cultivar CLHA02 (also known as RU1504197) is an elite Clearfield® (BASF, Ludwigshafen, Germany) long-grain rice (*Oryza sativa* L.) breeding line developed in Stoneville, Mississippi. CLHA02 was derived from the cross 'Rosemont'/3/'Mars'/'Newrex'//'Tebonnet'/4/'CL151', which was made in 2008. This cross utilized several publicly released commercial varieties, namely, Rosemont (Bollich et al., 1993), Mars (Johnston et al., 1979), Newrex (Bollich et al., 1980), and Tebonnet (Kuenzel et al., 1986), and utilized CL151 (Blanche et a., 2011) as donor for imidazolinone herbicide tolerance. CLHA02 was bred primarily using a modified pedigree method with several rounds of selection. Molecular markers were used for selecting/confirming grain quality, disease resistance, and herbicide tolerance traits in the later generations. The $F_1$ seeds of the multiparent cross were planted as '09G263' in the greenhouse in pots in 2009, and $F_2$, $F_3$, and $F_4$ panicles were grown as '11CLWN02624-2', '11CLPR29203-02', and '12CLPR12996' panicle rows, respectively, from 2010 to 2012. Bulked $F_5$ seeds from '12CLPR12996' were used for entering the derived line as '13CLOT1435' in the 2013 Observation Trial. The Pure Seed Nursery (PSS) were used as seed source for replicated and multilocation yield testing of the breeding line derivative, namely, as entry '14CLPYT174' in the 2014 Clearfield® Preliminary Yield Trial, as entry '15CLST018' in the 2015 Clearfield® State Yield Trial, as entry 'RU1504197' in the 2015, 2016, and 2018 multistate Uniform Rice Research Nurseries (URRN), and as entries '16OFVT032', '17OFVT013', '18OFVT013', and '19OFVT014' in the 2016, 2017, 2018, and 2019 multi-location Mississippi Official Rice Variety Trials, respectively. The results of these performance trials for CLHA02 are compared to those for other Clearfield® rice cultivars in the section titled "Performance Trial Results" below. Panicles were then selected from a 2018 head-to-row seed production plot in Stoneville for use in breeder seed production in 2019 following standard protocols.

CLHA02 is early maturing, semidwarf, lodging-resistant, and has very high and stable yield in the Mississippi Delta. The amylose content of CLHA02 is high (26.3%) and its amylose type is L202, such that it is softer when cooked than typical high-amylose varieties like 'CL163' and 'Thad'. Nonetheless, CLHA02 has an intermediate gelatinization temperature typical of southern US long-grain varieties. It has a weak rapid visco analyser (RVA) pasting profile, like 'Cheniere', in contrast to the strong pasting profile of CL163 and Thad. Therefore, CLHA02 is a unique Clearfield® elite line in terms of its cereal chemistry. It will be highly suitable for high amylose rice markets that prefer cooked rice that is softer and for processing industry users that require high amylose rice with the L202-type cereal chemistry. CLHA02 is nonaromatic.

In four years of official variety testing (2016 to 2019) involving 27 trials, CLHA02 was always in the top five among all Clearfield® entries for yield every year. It yielded an average of 219 bushels per acre (bu/A) or 9636 pounds per acre (lbs/A) across years and locations. The yield of CLHA02 was 10% over the average yield of CL151 (200 bu/A), 3% over that of 'CL153' (214 bu/A), and 7% over that of CL163 (205 bu/A). Moreover, CLHA02 also showed more stable yield performance than CL151, CL153, and CL163 over the 4-year testing period, outyielding or having comparable yields as these commercial Clearfield® varieties across key rice growing counties of Mississippi.

CLHA02 has excellent milling qualities (whole milled at 57% and total milled at 69%) that are comparable to those of CL151, CL153, and CL163. Its average grain chalkiness in the 4-year official variety trials (9.1%) as well as in a separate 2-year USDA grain quality evaluation (3.8%) was better than that of CL151 and CL163, but inferior to that of CL153 (6.1% and 2.2%, respectively). Grain length of CLHA02 whole milled rice (6.37 mm) was comparable to that of CL151 (6.35 mm) but shorter than that of CL153 and CL163 (both 6.71 mm). Its grain width (2.21 mm) was higher than that of CL151, CL153, and CL163. As a result, CLHA02 has a lower grain length-to-width ratio (2.89) compared to CL153 (3.28). The thousand-seed weight for CLHA02 (24.7 g) is less than that of CL151 (25.4 g), CL153 (25.4 g), and CL163 (26.2 g). As a result, the number of seeds of CLHA02 per pound (18,500) is greater than that of all three of these commercial Clearfield® varieties.

CLHA02 (38 in.) is one inch shorter than CL151 and CL153 and is two inches shorter than CL163. Its 87 days-to-50% heading is the same as CL153, 2 days earlier than CL163, and 2 days later than CL151. CLHA02 had zero or close to zero % average lodging in both the 4-year Mississippi (0.8%) and 2-year US Mid-south (0%) multi-location trials, which is superior to CL151 (17.7%; 6%), CL153 (7.2%; 0%), and CL163 (19.4; 3%). Its early vigor rating (5.0) is the same as that of CL163 but lower than that of CL151 and CL153 (both 4.0). In a controlled study of 64 rice genotypes (Reddy et al., 2021), CLHA02 was among only eight that were classified as 'very highly cold tolerant', which is superior to the 'high cold tolerance' ratings of CL151 and CL163.

CLHA02 has the Pik (Km) gene for resistance to rice blast disease caused by *Pyricularia grisea* (Cooke) Sacc. In the URRN, it was given a blast disease score of 0 which was same as CL163 but better than CL151 (2.5) and CL153 (0.5). CLHA02 showed similar or better reactions compared to CL151 to 8 of 11 different blast pathogen races. Moreover, in the URRN, it was rated as moderately susceptible (5.8) to sheath blight caused by *Rhizoctonia solani* Kühn, which is higher or better than CL151 (6.4) and CL163 (6.7). CLHA02 had an average field rating of intermediate (5.0) for bacterial panicle blight caused by *Burkholderia glumae*, which is lower than or inferior to CL151, CL153, and CL163, but was rated higher (2.0) than CL151 (4.5), CL153 (4.0), and CL163 (2.5) in two artificially inoculated screenings for the disease.

The leaves, lemma, and palea of CLHA02 are glabrous. The spikelet is straw-colored, and the grain is non-aromatic. Variants observed and removed from seed production plots were primarily taller or later-flowering. The few other variants included any combination of the following: pubescent, earlier, shorter, medium-grain and intermediate grain types, and grain with awn. The total number of variants numbered less than 1 per 5,000 plants. The cultivar has thus shown relative uniformity and stability.

The above-mentioned characteristics of rice cultivar CLHA02 are based primarily on data collected in Stoneville, Mississippi and are summarized in Table 1.

TABLE 1

Cultivar description.

| Characteristic | Cultivar CLHA02 |
|---|---|
| Grain type: | Long |
| Days to maturity (seeding to 50% heading): | 87 |
| Culm | |
| Angle (degrees from perpendicular after flowering): | Erect (less than 30°) |
| Length: | 96 cm |
| Internode color (after flowering): | Green |
| Strength (lodging resistance): | Strong (no lodging) |
| Flag leaf (after heading) | |
| Pubescence: | Glabrous |
| Leaf angle (after heading): | Erect |
| Blade color (at heading): | Green |
| Blade leaf sheath (at heading): | Green |
| Ligule | |
| Color (late vegetative stage): | White |
| Shape: | Cleft |
| Panicle | |
| Habit: | Erect |
| Length: | 17.46 cm |

TABLE 1-continued

Cultivar description.

| Characteristic | Cultivar CLHA02 |
|---|---|
| Type: | Compact |
| Exertion (near maturity): | 100% exerted |
| Threshability: | Easy |
| Shattering (at maturity): | Low (≤5%) |
| Grain (spikelet) | |
| Awns (after full heading): | Absent |
| Apiculus color (at maturity): | Straw |
| Apiculus color (after full heading): | Straw |
| Stigma color: | White |
| Lemma and palea color (at maturity): | Straw |
| Lemma and palea pubescence: | Glabrous |
| Grain (seed): | |
| Seed coat color: | Light brown |
| Scent: | Nonscented |
| Shape class (length/width ratio) | |
| Paddy: | Long (3.4:1 and more) |
| Brown: | Long (3.1:1 and more) |
| Milled: | Long (3.0:1 and more) |
| Gelatinization temperature type: | Intermediate |
| Disease resistance: | |
| Sheath blight (*Rhizoctonia solani*): | Intermediate |
| Bacterial panicle blight: | Moderately resistant |

Performance Trial Results:

TABLE 2

Yield of CLHA02 and Clearfield ® check varieties in MS Official Variety Trials (4 years, 27 trials/locations), 2016-2019.

| Entry | Clarksdale/ Tutwiler | Hollandale bu/A | Ruleville bu/A | Shaw/ Drew bu/A | Stoneville bu/A | Tunica bu/A | Choctaw/ Cleveland bu/A | Across Locations bu/A | CLHA02 Average Advantage bu/A | % |
|---|---|---|---|---|---|---|---|---|---|---|
| CLHA02 | 233 | 229 | 222 | 216 | 169 | 230 | 240 | 219 | | |
| CL151 | 225 | 197 | 205 | 194 | 146 | 224 | 207 | 200 | 20 | 10 |
| CL153 | 235 | 227 | 212 | 201 | 145 | 236 | 248 | 214 | 5 | 3 |
| CL163 | 237 | 201 | 229 | 185 | 160 | 207 | 212 | 205 | 15 | 7 |
| All CL Entries | 232 | 214 | 214 | 211 | 157 | 219 | 225 | 210 | 9 | 4 |

TABLE 3

Milling, agronomic, and seed traits for CLHA02 and Clearfield ® check varieties in MS Official Variety Trials (4 years; 28 trials), 2016-2019.

| Entry | Whole Milled Rice % | Total Milled Rice % | Chalk[1] % | Plant Height in | 50% Heading[2] days | Lodging[3] % | 1000 Seed Weight[4] g | Bushel Weight lb | Seeds/ pound 1000x |
|---|---|---|---|---|---|---|---|---|---|
| CLHA02 | 57.1 | 69.1 | 9.1 | 38.0 | 87.4 | 0.8 | 24.7 | 42.9 | 18.5 |
| CL151 | 56.6 | 70.0 | 11.3 | 38.8 | 85.2 | 17.7 | 25.4 | 40.9 | 18.1 |
| CL153 | 59.4 | 70.1 | 6.1 | 39.0 | 87.0 | 7.2 | 25.4 | 40.8 | 18.2 |
| CL163 | 57.7 | 68.9 | 9.8 | 40.5 | 88.7 | 19.4 | 26.6 | 39.6 | 17.3 |
| All CL Entries | 56.2 | 69.3 | 9.4 | 39.1 | 87.2 | 7.2 | 26.2 | 40.7 | 17.6 |

[1] Winseedle chalk measurement.
[2] Days after emergence.
[3] Percent of plot that was lodged.
[4] Weight of 1,000 kernels.

TABLE 4

Cereal chemistry profiles for CLHA02 and Clearfield ® check varieties based on Grain Quality Evaluation of URRN Entries (2 years), Dale Bumpers National Rice Research Center, USDA, Stuttgart, AR; 2015-2016.

| | Quality Phenotype | | | | | | |
|---|---|---|---|---|---|---|---|
| | Amylose | | | | RVA Parameters | | |
| Entry | Content (%) | ASV AVG | ASV_min | ASV_max | Peak | Trough | Break- down |
| CLHA02 | 26.3 | 4.0 | 4.0 | 4.0 | 202.6 | 98.9 | 103.8 |
| CL151 | 19.8 | 3.7 | 3.0 | 4.0 | 280.1 | 138.4 | 141.7 |

TABLE 4-continued

Cereal chemistry profiles for CLHA02 and Clearfield ® check
varieties based on Grain Quality Evaluation of URRN Entries (2 years),
Dale Bumpers National Rice Research Center, USDA, Stuttgart, AR; 2015-2016.

| CL153 | 21.1 | 4.3 | 4.0 | 5.0 | 274.0 | 142.0 | 132.1 |
| CL163 | 26.1 | 4.1 | 4.0 | 4.5 | 295.5 | 175.9 | 119.7 |

| | RVA Parameters | | | Quality Markers | | | |
|---|---|---|---|---|---|---|---|
| Entry | Final Visc | Setback from Trough | Setback from Peak | Amylose Type | RVA Profile | Gel Temp | Aroma |
| CLHA02 | 239.1 | 140.2 | 36.5 | L202 | Weak | Intermed | None |
| CL151 | 287.9 | 149.6 | 7.9 | Interned | — | Intermed | None |
| CL153 | 284.8 | 142.8 | 10.7 | Interned | — | Intermed | None |
| CL163 | 347.7 | 171.8 | 51.9 | High | Strong | Intermed | None |

TABLE 5

Grain dimensions and chalk parameters for CLHA02 and Clearfield ® check varieties
based on Grain Quality Evaluation of URRN Entries (2 years), DBNRRC, USDA, Stuttgart, AR; 2015-2016.

| | Grain Dimensions and Chalk Parameters | | | | | | | | |
|---|---|---|---|---|---|---|---|---|---|
| Entry | WinSeedle # of Seeds | Straight Length (mm) | Std Dev (Straight Length) | Straight Width (mm) | Std Dev (Straight Width) | Length/Width Ratio | Std Dev L/W ratio | % Chalk in Milled Rice | Std Dev (% Chalk) |
| CLHA02 | 170 | 6.37 | 0.37 | 2.21 | 0.11 | 2.89 | 0.20 | 3.78 | 8.13 |
| CL151 | 174 | 6.35 | 0.33 | 2.15 | 0.09 | 2.96 | 0.18 | 8.51 | 12.38 |
| CL153 | 190 | 6.71 | 0.39 | 2.05 | 0.10 | 3.28 | 0.22 | 2.24 | 4.96 |
| CL163 | 166 | 6.71 | 0.43 | 2.19 | 0.12 | 3.06 | 0.22 | 4.51 | 9.11 |

TABLE 6

Reaction of CLHA02 and Clearfield ® check varieties to sheath
blight and bacterial panicle blight diseases in the 2015 and 2016 URRN
at locations in Mississippi (MS), Louisiana (LA) and Arkansas (AR).

| | Sheath Blight | | | | | | | Bacterial Panicle Blight | | | |
|---|---|---|---|---|---|---|---|---|---|---|---|
| Entry | LA 2015 | MS 2015 | LA 2016 | Average | LA 2015 | AR 2016 | LA 2016 | Natural Infection Average | AR 2016 Artificial April | AR 2016 Artificial May | Artificial Infection Average |
| CLHA02 | 6.5 | 5.3 | 5.5 | 5.8 | 5.0 | 5.0 | 5.0 | 5.0 | 1.0 | 3.0 | 2.0 |
| CL151 | 6.3 | 7.3 | 5.5 | 6.4 | 5.0 | 3.0 | 4.5 | 4.2 | 4.0 | 5.0 | 4.5 |
| CL153 | 6.8 | 5.3 | 4.8 | 5.6 | 4.8 | 3.0 | 2.9 | 3.6 | 3.0 | 5.0 | 4.0 |
| CL163 | 6.5 | 7.0 | 6.5 | 6.7 | 1.5 | 4.0 | 4.0 | 3.2 | 1.0 | 4.0 | 2.5 |

*Disease Severity Scale 0 (Absent or No Disease) to 9 (Severe or Maximum Disease)

TABLE 7

Reaction of CLHA02 and Clearfield ® check varieties to rice
blast disease in the 2016 URRN in Louisiana (LA) and to different races
of the blast pathogen in greenhouse evaluations conducted in Arkansas (AR).

| | Blast LA | AR 2015 GREENHOUSE NURSERY | | | | | | | | |
|---|---|---|---|---|---|---|---|---|---|---|
| Entry | 2016 | IB-49 | IC-17 | IB-49 | IG-1 | IB33 | IB54 | IB-49 | IE-1 | IB-1 | IC-1 | Race K |
| CLHA02 | 0.0 | 4 | 5 | 6 | 0 | 6 | 0 | 6 | 5 | 4 | 5 | 6 |
| CL151 | 2.5 | 4 | 6 | 6 | 0 | 4 | 0 | 7 | 5 | 3 | 4 | 7 |
| CL153 | 0.5 | 0 | 0 | 0 | 0 | 3 | 0 | 0 | 0 | 0 | 0 | 5 |

*Disease Severity Scale 0 (Absent or No Disease) to 9 (Severe or Maximum Disease)

TABLE 8

Average yield by location of CLHA02, Clearfield ® check varieties,
and other Clearfield ®-type entries in the MS Official Variety Trials, 2016.

| Entry | Clarksdale/ Tutwiler bu/A | Hollandale bu/A | Ruleville bu/A | Shaw/ Drew bu/A | Stoneville bu/A | Tunica bu/A | Choctaw/ Cleveland bu/A | Average bu/A | Stability lower value is better | Rank in CL Grp |
|---|---|---|---|---|---|---|---|---|---|---|
| CLHA02 | 194 | 197 | 198 | 223 | 147 | 209 | 213 | 197 | 12 | 3 |
| CL151 | 189 | 151 | 185 | 222 | 103 | 246 | 176 | 182 | 26 | 9 |
| CL153 | 212 | 176 | 213 | 233 | 105 | 234 | 200 | 196 | 23 | 5 |
| CL163 | 214 | 174 | 239 | 208 | 163 | 199 | 176 | 196 | 14 | 4 |
| CL Entries Mean (n = 11) | 203 | 178 | 204 | 231 | 127 | 210 | 197 | 193 | 20 | |
| Trial LSD | 23 | 26 | 34 | 29 | 28 | 24 | 34 | | | |
| Trial CV | 7% | 8% | 10% | 8% | 12% | 7% | 9% | | | |

TABLE 9

Average milling, agronomic, and seed traits for CLHA02, Clearfield ® check varieties,
and other Clearfield ®-type entries in seven locations of the MS Official Variety Trials, 2016.

| Entry | Whole Milled Rice % | Total Milled Rice % | Chalk[5] % | Bushel Weight lb | Plant Height in | 50% Heading[6] days | Lodging[7] % | Lodging[8] (1-5) | 1000 Seed Weight[9] g | Seeds/ pound no. |
|---|---|---|---|---|---|---|---|---|---|---|
| CLHA02 | 58.9 | 70.0 | 10.1 | 44.0 | 37 | 84 | 1 | 1 | 23.0 | 19770 |
| CL151 | 58.3 | 70.5 | 10.7 | 40.8 | 39 | 83 | 21 | 2 | 22.0 | 20636 |
| CL153 | 61.2 | 70.5 | 5.5 | 40.6 | 41 | 86 | 15 | 2 | 21.6 | 21046 |
| CL163 | 58.1 | 69.2 | 9.6 | 39.8 | 42 | 89 | 27 | 2 | 22.8 | 19925 |
| CL Mean | 58 | 70 | 9 | 41 | 40 | 85 | 12 | 2 | 23 | 20032 |
| LSD | 3.4 | 1.4 | 1.6 | 1.4 | 1.7 | 5.2 | 14.0 | 0.5 | 1.0 | |
| CV | 7.9 | 2.7 | 28.5 | 4.4 | 5.5 | 8.1 | | | | |

[5]Winseedle chalk measurement.
[6]Days after emergence.
[7]Percent of plot that was lodged.
[8]Severity of lodging: 1 = plants totally erect, 5 = plants completely on ground.
[9]Weight of 1000 kernels.

TABLE 10

Average and by location yield of CLHA02, Clearfield ® check varieties,
and other Clearfield ®-type entries in the MS Official Variety Trials, 2017.

| Entry | Clarksdale/ Tutwiler bu/A | Hollandale bu/A | Ruleville bu/A | Shaw/ Drew bu/A | Stoneville bu/A | Tunica bu/A | Choctaw/ Cleveland bu/A | Average bu/A | Stability lower value is better | Rank in CL Grp |
|---|---|---|---|---|---|---|---|---|---|---|
| CLHA02 | 218 | 243 | 264 | 214 | 137 | 241 | 248 | 223 | 19 | 4 |
| CL151 | 251 | 211 | 232 | 180 | 141 | 231 | 277 | 218 | 21 | 6 |
| CL153 | 247 | 244 | 249 | 176 | 120 | 248 | 276 | 223 | 25 | 5 |
| CL163 | 224 | 190 | 272 | 133 | 107 | 211 | 230 | 195 | 30 | 11 |
| CL Emtries Mean (n = 12) | 235 | 228 | 242 | 198 | 140 | 218 | 246 | 215 | 20 | |
| Trial LSD | 30 | 41 | 33 | 22 | 36 | 31 | 23 | | | |
| Trial CV | 7% | 10% | 8% | 6% | 15% | 8% | 6% | | | |

TABLE 11

Average milling, agronomic, and seed traits for CLHA02, Clearfield ® check varieties,
and other Clearfield ®-type entries in seven locations of the MS Official Variety Trials, 2017.

| Entry | Whole Milled Rice % | Total Milled Rice % | Chalk[10] % | Bushel Weight lb | Plant Height in | 50% Heading[11] days | Lodging[12] % | Lodging[13] (1-5) | 1000 Seed Weight[14] g | Seeds/ pound no. |
|---|---|---|---|---|---|---|---|---|---|---|
| CLHA02 | 59.1 | 70.7 | 7.5 | 44.4 | 38 | 97 | 0 | 1 | 23.0 | 19709 |
| CL151 | 57.7 | 70.9 | 11.3 | 42.7 | 38 | 95 | 17 | 2 | 23.2 | 19575 |
| CL153 | 59.5 | 70.8 | 6.7 | 42.3 | 38 | 97 | 8 | 1 | 23.5 | 19325 |

TABLE 11-continued

Average milling, agronomic, and seed traits for CLHA02, Clearfield ® check varieties, and other Clearfield ®-type entries in seven locations of the MS Official Variety Trials, 2017.

| Entry | Whole Milled Rice % | Total Milled Rice % | Chalk[10] % | Bushel Weight lb | Plant Height in | 50% Heading[11] days | Lodging[12] % | Lodging[13] (1-5) | 1000 Seed Weight[14] g | Seeds/ pound no. |
|---|---|---|---|---|---|---|---|---|---|---|
| CL163 | 59.7 | 70.1 | 9.4 | 40.1 | 40 | 97 | 33 | 2 | 24.8 | 18322 |
| CL Emtries Mean (n = 12) | 58 | 71 | 10 | 43 | 38 | 97 | 7 | 1 | 24 | 19019 |
| Trial LSD | 4.9 | 1.2 | 2.0 | 2.2 | 1.8 | 4.0 | 16.5 | 0.6 | 0.7 | |
| Trial CV | 11.4 | 2.3 | 34.0 | 6.8 | 5.9 | 5.0 | | | | |

[10] Winseedle chalk measurement;
[11] Days after emergence;
[12] Percent of plot that was lodged;
[13] Severity of lodging: 1 = plants totally erect, 5 = plants completely on ground;
[14] Weight of 1000 kernels.

TABLE 12

Average and by location yield of CLHA02, Clearfield ® check varieties, and other Clearfield ®-type entries in the MS Official Variety Trials, 2018.

| Entry | Clarksdale/ Tutwiler bu/A | Hollandale bu/A | Ruleville bu/A | Shaw/ Drew bu/A | Stoneville bu/A | Tunica bu/A | Choctaw/ Cleveland bu/A | Average bu/A | Stability ower value is better | Rank in CL Grp |
|---|---|---|---|---|---|---|---|---|---|---|
| CLHA02 | 275 | 200 | 208 | 183 | 200 | 260 | 258 | 226 | 15 | 3 |
| CL151 | 277 | 175 | 192 | 146 | 185 | 195 | 168 | 191 | 20 | 13 |
| CL153 | 295 | 215 | 185 | 170 | 165 | 238 | 269 | 220 | 21 | 7 |
| CL163 | 258 | 190 | 195 | 160 | 183 | 209 | 229 | 203 | 15 | 11 |
| CL Entries Mean (n = 15) | 267 | 190 | 193 | 180 | 181 | 230 | 233 | 210 | 17 | |
| Trial LSD | 34 | 24 | 27 | 41 | 22 | 30 | 43 | | | |
| Trial CV | 7.4% | 14.8% | 16.6% | 25.5% | 7.4% | 18.4% | 10.5% | | | |

TABLE 13

Average milling, agronomic, and seed traits for CLHA02, Clearfield ® check varieties, and other Clearfield ®-type entries in seven locations of the MS Official Variety Trials, 2018.

| Entry | Whole Milled Rice % | Total Milled Rice % | Chalk[15] % | Bushel Weight lb | Plant Height in | 50% Heading[16] days | Lodging[17] % | Lodging[18] (1-5) | 1000 Seed Weight[19] g | Seeds/ pound no. |
|---|---|---|---|---|---|---|---|---|---|---|
| CLHA02 | 52.8 | 68.2 | 9.6 | 39.3 | 38 | 83 | 2 | 1 | 24.8 | 18317 |
| CL151 | 50.6 | 69.4 | 13.6 | 37.3 | 40 | 80 | 33 | 2 | 26.9 | 16904 |
| CL153 | 54.8 | 69.3 | 6.8 | 37.4 | 38 | 81 | 5 | 1 | 26.4 | 17178 |
| CL163 | 53.8 | 67.9 | 10.9 | 36.4 | 41 | 85 | 18 | 2 | 27.7 | 16381 |
| CL Entries Mean (n = 15) | 51 | 68 | 11 | 37 | 39 | 82 | 10 | 1 | 28 | 16505 |
| Trial LSD | 6.9 | 1.3 | 2.7 | 7.9 | 2.0 | 3.8 | 17.8 | 0.6 | 1.8 | |
| Trial CV | 18.1 | 2.5 | 38.3 | 28.4 | 6.8 | 6.2 | | | | |

[15] Winseedle chalk measurement.
[16] Days after emergence.
[17] Percent of plot that was lodged.
[18] Severity of lodging: 1 = plants totally erect, 5 = plants completely on ground.
[19] Weight of 1000 kernels.

TABLE 14

Average and by location yield of CLHA02, Clearfield ® check varieties, and other Clearfield ®-type entries in the MS Official Variety Trials, 2019.

| Entry | Clarksdale/ Tutwiler bu/A | Hollandale bu/A | Ruleville bu/A | Shaw/ Drew bu/A | Stoneville bu/A | Tunica bu/A | Choctaw/ Cleveland bu/A | Average bu/A | Stability lower value is better | Rank in CL Grp |
|---|---|---|---|---|---|---|---|---|---|---|
| CLHA02 | 244 | 275 | 217 | 244 | 192 | 213 | | 231 | 13 | 5 |
| CL151 | 185 | 249 | 212 | 228 | 157 | 222 | | 209 | 16 | 14 |
| CL153 | 188 | 273 | 202 | 226 | 188 | 225 | | 217 | 15 | 13 |

TABLE 14-continued

Average and by location yield of CLHA02, Clearfield ® check varieties,
and other Clearfield ®-type entries in the MS Official Variety Trials, 2019.

| Entry | Clarksdale/ Tutwiler bu/A | Hollandale bu/A | Ruleville bu/A | Shaw/ Drew bu/A | Stoneville bu/A | Tunica bu/A | Choctaw/ Cleveland bu/A | Average bu/A | Stability lower value is better | Rank in CL Grp |
|---|---|---|---|---|---|---|---|---|---|---|
| CL163 | 254 | 250 | 209 | 238 | 187 | 209 | | 225 | 12 | 10 |
| CL Entries Mean (n = 16) | 225 | 260 | 216 | 233 | 183 | 220 | | 223 | 13 | |
| Trial LSD | 35 | 27 | 37 | 20 | 19 | 31 | | | | |
| Trial CV | 9.3% | 6.4% | 10.6% | 5.1% | 6.4% | 8.3% | | | | |

TABLE 15

Average milling, agronomic, and seed traits for CLHA02, Clearfield ® check varieties,
and other Clearfield ®-type entries in seven locations of the MS Official Variety Trials, 2019.

| Entry | Whole Milled Rice % | Total Milled Rice % | Chalk[20] % | Bushel Weight lb | Plant Height in | 50% Heading[21] days | Lodging[22] % | Lodging[23] (1-5) | 1000 Seed Weight[24] g | Seeds/ pound no. |
|---|---|---|---|---|---|---|---|---|---|---|
| CLHA02 | 57.6 | 67.5 | 9.3 | 43.9 | 39 | 85 | 0 | 1 | 28.0 | 16231 |
| CL151 | 59.8 | 69.3 | 9.4 | 42.6 | 38 | 82 | 0 | 1 | 29.5 | 15367 |
| CL153 | 62.1 | 69.7 | 5.3 | 42.8 | 39 | 84 | 0 | 1 | 30.0 | 15148 |
| CL163 | 59.1 | 68.2 | 9.0 | 42.2 | 40 | 84 | 0 | 1 | 31.0 | 14638 |
| CL Entries Mean (n = 16) | 58 | 68 | 8 | 42 | 39 | 85 | 0 | 1 | 30 | 14963 |
| Trial LSD | 2.3 | 2.3 | 1.7 | 1.8 | 1.5 | 3.9 | 4.8 | 0.1 | 1.2 | |
| Trial CV | 5.4 | 4.5 | 30.7 | 5.6 | 5.0 | 6.1 | | | | |

[20]Winseedle chalk measurement.
[21]Days after emergence.
[22]Percent of plot that was lodged.
[23]Severity of lodging: 1 = plants totally erect, 5 = plants completely on ground;
[24]Weight of 1000 kernels.

TABLE 16

US Midsouth performance of CLHA02 and Clearfield ® check varieties
for agronomic and milling traits based on 2 years (2015 and 2016) of URRN
data from Arkansas (AR), Louisiana (LA), Mississippi (MS) and Texas (TX).

| | Plant Height (cm) | | | | | Days to 50% Heading | | | | | % Lodging | | | | |
|---|---|---|---|---|---|---|---|---|---|---|---|---|---|---|---|
| Variety | AR | LA | MS | TX | Ave | AR | LA | MS | TX | Ave | AR | LA | MS | TX | Ave |
| CLHA02 | 102 | 93 | 101 | 85 | 95 | 91 | 82 | 82 | 80 | 84 | 0 | 0 | 0 | 0 | 0 |
| CL151 | 108 | 95 | 109 | 83 | 99 | 90 | 81 | 81 | 82 | 84 | 0 | 0 | 24 | 0 | 6 |
| CL153 | 109 | 94 | 108 | 84 | 99 | 93 | 84 | 81 | 79 | 84 | 0 | 0 | 0 | 0 | 0 |
| CL163 | 116 | 101 | 112 | 86 | 104 | 97 | 83 | 84 | 79 | 86 | 0 | 0 | 10 | 0 | 3 |

| | Vigor | | | % Head Rice | | | | | % Total Rice | | | | |
|---|---|---|---|---|---|---|---|---|---|---|---|---|---|
| Variety | AR | LA | Ave | AR | LA | MS | TX | Ave | AR | LA | MS | TX | Ave |
| CLHA02 | 5 | 5 | 5 | 64 | 64 | 65 | 56 | 62 | 70 | 73 | 71 | 69 | 71 |
| CL151 | 4 | 3 | 4 | 65 | 64 | 64 | 59 | 63 | 70 | 73 | 72 | 71 | 71 |
| CL153 | 4 | 4 | 4 | 60 | 67 | 65 | 63 | 64 | 67 | 73 | 72 | 71 | 71 |
| CL163 | 4 | 5 | 5 | 59 | 58 | 64 | 62 | 61 | 65 | 71 | 70 | 70 | 69 |

TABLE 17

Grain dimensions and weight of CLHA02 and Clearfield® check varieties, DREC, Stoneville MS, 2020.

| Variety | Length (L; mm) | Width (W; mm) | L/W Ratio | Weight (mg) |
|---|---|---|---|---|
| Paddy Rice | | | | |
| CLHA02 | 9.0 | 2.7 | 3.33 | 24.2 |
| CL151 | 9.1 | 2.6 | 3.50 | 22.6 |
| CL153 | 9.7 | 2.6 | 3.73 | 22.2 |
| CL163 | 9.7 | 2.6 | 3.73 | 24.2 |
| Brown Rice | | | | |
| CLHA02 | 7.2 | 2.4 | 3.00 | 20.2 |
| CL151 | 7.2 | 2.3 | 3.13 | 18.4 |
| CL153 | 7.7 | 2.2 | 3.50 | 20.6 |
| CL163 | 7.6 | 2.2 | 3.45 | 19.1 |
| Milled Rice | | | | |
| CLHA02 | 6.4 | 2.1 | 3.05 | 17.6 |
| CL151 | 6.4 | 2.2 | 2.95 | 16.5 |
| CL153 | 6.7 | 2.1 | 3.27 | 17.4 |
| CL163 | 6.7 | 2.2 | 3.06 | 19.0 |

Developmental History:

TABLE 18

Developmental history of CLHA02.

| Year | Generation | ID in Activity/Yield Test[25] (Activity/Yield Test/Seed Production) | Seed Source[26] |
|---|---|---|---|
| 2008 | F0 | RSMT/3/MARS/NWRX//TBNT/4/CL151 (Initial Cross) | — |
| 2009 | F1 | 09G263 (Greenhouse seed increase) | 09G 263 |
| 2010-2011 | F2 | 11CLWN02624-2 (Puerto Rico Winter Nursery) | 10CLF2 00027 |
| 2011 | F3 | 11CLPR29203-02 (Clearfield® Panicle Rows) | 11CLWN02624-2 |
| 2012 | F4 | 12CLPR12996 (Clearfield® Panicle Rows) | 11CLPR29203-02 |
| 2013 | F5 | 13CLOT1435 (Clearfield® Observational Trial- CLOT)) | 12CLPR12996 |
| 2014 | F6 | 14CLPYT174 (Clearfield® Preliminary Yield Trial- CLPYT)) | 13CLPSS1379 |
| 2015 | F7 | RU1504197/15CLST018 (Clearfield® State Yield Trial- CLST) (Uniform Rice Research Nursery- URRN) | 14CLPSS0187 |
| 2016 | F8 | RU1504197/16OFVT032 (Uniform Rice Research Nursery- URRN) (Official Rice Variety Trial- OFVT) | 15CLPSS0007 |
| 2017 | F9 | 17OFVT013 (Official Rice Variety Trial- OFVT) | 16CLPSS0006 |
| 2018 | F10 F11 | RU1504197/18OFVT013 (Uniform Rice Research Nursery- URRN) (Official Rice Variety Trial- OFVT) (Panicle selection in Puerto Rico) Head Row Seed Production in Stoneville | 17CLPSS0004 P. Rico Panicles |
| 2019 | F12 F12 | 19OFVT014 (Official Rice Variety Trial- OFVT) Breeder Seed Production in Stoneville | 18CLPSS0003 18Head Rows |

[25]Testing or breeding activity where the breeding line was included that year
[26]Where the seeds used for the testing or breeding activity came from (e.g., pure seed source or PSS)

Herbicide Resistance:

CLHA02 comprises the AHASL-S653(At)N trait (also referred to herein as the "S653N trait") for herbicide tolerance. AHASL is an abbreviation for acetohydroxyacid synthase (AHAS) large subunit (L). This trait is the result of a mutation in the rice AHASL gene that changed the 627th codon from AGY (encoding Ser) to AAY (encoding Asn). This mutation was generated using traditional, chemical mutagenesis. See U.S. Pat. No. 7,399,905, which is incorporated by reference herein. The position numbering of plant AHASL polypeptides is standardized to the *Arabidopsis thaliana* AHASL sequence. When the rice and *A. thaliana* AHASL amino acid sequences are aligned, rice position Ser627 corresponds to *A. thaliana* position S653. In formal usage, the numbering system is indicated immediately following the position number, e.g., S653 (A t)N. Accordingly, the herbicide tolerance trait found in CLHA02 rice is referred to as the AHASL-S653(At)N trait.

Clearfield® (CL) rice varieties are resistant to imidazolinone herbicides (WSSA Group 2), which control weeds by inhibiting the enzyme acetohydroxyacid synthase (AHAS), also called acetolactate synthase (ALS). CL rice was developed through mutagenesis of the ALS locus using traditional breeding techniques and is not considered genetically modified. The herbicide-resistance trait of this rice makes it particularly useful in regions where there is a need to control weedy rice and other tough grasses. Thus, the majority of rice cultivars planted in the southern United States are CL inbred or hybrid.

The plants of rice cultivar CLHA02 have increased tolerance or resistance to AHAS-inhibiting herbicides, particularly imidazolinone herbicides. Thus, the plants of rice cultivar CLHA02 are herbicide-tolerant or herbicide-resistant rice plants. An "herbicide-tolerant" or a "herbicide-resistant" rice plant is a rice plant that is tolerant or resistant to at least one herbicide at a level that would normally kill, or inhibit the growth of, a normal or wild-type rice plant. For the present invention, the terms "herbicide-tolerant" and "herbicide-resistant" are used interchangeably and are intended to have an equivalent meaning and an equivalent scope. Similarly, the terms "herbicide-tolerance" and "herbicide-resistance" are used interchangeably and are intended to have an equivalent meaning and an equivalent scope. Likewise, the terms "imidazolinone-tolerant" and "imidazolinone-resistant" are used interchangeably and are intended to be of an equivalent meaning and an equivalent scope as the terms "imidazolinone-tolerance" and "imidazolinone-resistance", respectively.

Accordingly, the present disclosure provides rice seeds treated with an AHAS-inhibiting herbicide. AHAS-inhibiting herbicides include, without limitation, imidazolinone herbicides, sulfonylurea herbicides, triazolopyrimidine herbicides, pyrimidinyloxybenzoate herbicides, sulfonylaminocarbonyltriazolinone herbicides, and mixtures thereof. In some embodiments, the AHAS-inhibiting herbicide is an imidazolinone herbicide or a mixture of two or more imidazolinone herbicides. Suitable imidazolinone herbicides include, without limitation, PURSUIT®, NEWPATH® (imazethapyr); CADRE®, MASTERKEY® (imazapic); RAPTOR®, BEYOND®, SWEEPER® (imazamox), SCEPTER® (imazaquin), ASSERT® (imazethabenz), ARSENAL® (imazapyr), and any salts, esters, or derivatives of any of the aforementioned herbicides (e.g., imazamox-ammonium, imazamox-sodium, imazethapyr-ammonium, imazapyr-isopropylammonium, imazapic-ammonium, imazaquin-ammonium, imazaquin-methyl, imazaquin-sodium). In some embodiments, the AHAS-inhibiting herbicide comprises a mixture of two or more of the aforementioned herbicides, salts, esters or derivatives thereof, for example, imazapyr/imazamox (ODYSSEY). More specifically, the imidazolinone herbicide can be selected from, but is not limited to, 2-(4-isopropyl-4-methyl-5-oxo-2-imidiazolin-2-yl)-nicotinic acid, [2-(4-isopropyl)-4-][methyl-5-oxo-2-imidazolin-2-yl)-3-quinolinecarboxylic]acid, [5-ethyl-2-(4-isopropyl-]4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, [2-(4-isopropyl-4-methyl-5-oxo-2-]imidazolin-2-yl)-5-methylnicotinic acid, and a mixture of methyl[6-(4-isopropyl-4-]methyl-5-oxo-2-imidazolin-2-yl)-m-toluate and methyl[2-(4-isopropyl-4-methyl-5-]oxo-2-imidazolin-2-yl)-p-toluate. Examples of particular formulations and appropriate application times and rates are listed below:

Beyond® (12.1% imazamox-NH4; 11b ae/gallon)≤3, ≤2, or 1 POST applications (respectively following 0, 1, or 2 applications each of 70-105 g AI/ha imazethapyr) of 34.7-52.7 g AI/ha imazamox each, up to an annual maximum of 131.1, 87.4, or 52.7 g AI/ha imazamox, respectively.

Beyond® Plus (3.04% imazamox; 33.3 g AI/L) 1 or 2 POST applications of 36.6 (36.63) g AI/ha imazamox each, up to an annual maximum of 73.26 g AI/ha imazamox Newpath® (22.87% imazethapyr-NH4; 21b ae/gallon) 2 applications: 1 PRE & 1 POST—or -2 POST of 70-105 g AI/ha imazethapyr each.

Clearpath® (13.02% imazethapyr acid+61.98% quinclorac; 130.2 g IMI AI/kg) 1 PRE or POST application of 73-105 g AI/ha imazethapyr (with 347-500 g AI/ha quinclorac)

Kifix® (17.5% imazapic acid+52.5% imazapyr acid; 175 g AI/kg+525 g AI/kg, respectively) 2 applications: 1 PRE & 1 POST of 140 g/ha Kifix® each=24.5 g AI/ha imazapic+73.5 g AI/ha imazapyr each.

Only (7.5% imazethapyr (ae)+2.5% imazapic (ae); 75 g AI/L+25 g AUL, respectively) 2 applications: 1 PRE of 56.25 g AI/ha imazethapyr+18.75 g AI/ha imazapic, and 1 POST of 37.5 g AI/ha imazethapyr+12.5 g AI/ha imazapic; or 1 POST application of 75 g AI/ha imazethapyr+25 g AI/ha imazapic.

Eurolightning® (3.3% imazamox acid+1.5% imazapyr acid; 33 g AI/L+15 g AI/L, respectively) 1 POST application of 2-2.5 L/ha Eurolightning®=66-82.5 g AI/ha imazamox+30-37.5 g AI/ha imazapyr.

Sweeper® (70% imazamox acid; 700 g AI/kg) 2 POST applications of 98 g AI/ha imazamox each.

Sweeper® Pro (12.10% imazamox acid; 119.7 g AI/L) 2 POST applications of 30-48 (47.8) g AI/ha imazamox each; or 1 POST application of 60-120 g AI/ha imazamox.

OnDuty® (52.5% imazapic+17.5% imazapyr; 525 g+175 g AI/kg, respectively) 1 POST application of 112.5 g AI/ha imazapic+37.5 g AI/ha imazapyr.

Masterkey® (70% imazapic; 700 g AI/kg) 2 applications: 1 PRE & 1 POST of 80.5 g AI/ha imazapic each.

A wide variety of herbicide formulations can be employed for protecting plants from weeds to enhance plant growth and reduce competition for nutrients. Customary formulations include solutions, emulsions, suspensions, dispersions, dusts, powders, pastes, and granules. The use form depends on the particular intended purpose. However, in each case, it should ensure a fine and even distribution of the compound. Aqueous use forms can be prepared from emulsion concentrates, pastes, or wettable powders (e.g., sprayable powders, oil dispersions) by adding water. To prepare emulsions, pastes, or oil dispersions, the substances, as such or dissolved in an oil or solvent, can be homogenized in water by means of a wetter, tackifier, dispersant or emulsifier. However, it is also possible to prepare concentrates that are suitable for dilution with water composed of active substance, wetter, tackifier, dispersant or emulsifier and, if appropriate, solvent or oil.

The herbicide formulations used with the present invention may comprise the AHAS-inhibiting herbicide at a concentration of from 0.01% to 95% by weight of active compound, preferably from 0.1 to 90% by weight. The AHAS-inhibiting herbicides should be employed in a purity of 90% to 100% by weight, preferably 95% to 100% by weight (according to NMR spectrum). For seed treatment purposes, formulations can be diluted 2-10 fold leading to concentrations in the range of 0.01% to 60% by weight of active compound, preferably 0.1 to 40% by weight.

The herbicide may be applied at pre-emergence, post-emergence, pre-planting, and/or at planting to control weeds in areas surrounding the rice plants described herein. The herbicide and herbicide formulations can be applied in accordance with conventional methods, for example, by spraying, irrigation, dusting, broadcast, drench, or the like. In some embodiments, the herbicide is applied by contacting the rice seeds before sowing or at seeding (e.g., in-furrow). In other embodiments, the herbicide is applied to the weeds and to the rice plant post-emergence, e.g., using over-the-top application.

An herbicide can be used by itself or as part of an herbicide formulation that contains other additives. Suitable additives include solvents, carriers, emulsifiers, surfactants, dispersants, preservatives, antifoaming agents, and colorants, binders, and gelling agents. Examples of suitable solvents include water, aromatic solvents (e.g., Solvesso products, xylene), paraffins (e.g., mineral oil fractions), alcohols (e.g., methanol, butanol, pentanol, benzyl alcohol), ketones (e.g., cyclohexanone, gamma-butyrolactone), pyrrolidones (NMP, NOP), acetates (glycol diacetate), glycols, fatty acid dimethylamides, fatty acids and fatty acid esters. In principle, solvent mixtures may also be used. Examples of suitable carriers are ground natural minerals (e.g., kaolins, clays, talc, chalk) and ground synthetic minerals (e.g., highly disperse silica, silicates). Suitable emulsifiers include nonionic and anionic emulsifiers (e.g., polyoxyethylene fatty alcohol ethers, alkylsulfonates, arylsulfonates). Examples of dispersants are lignin-sulfite waste liquors and methylcellulose. Suitable surfactants include alkali metal, alkaline earth metal, and ammonium salts (e.g., of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates, fatty acids, and sulfated fatty alcohol glycol ethers), condensates of sulfonated naphthalene and naphthalene derivatives with formaldehyde, condensates of naphthalene or of naphthalenesulfonic acid with phenol and formaldehyde, polyoxyethylene octylphenol ether, ethoxylated isooctylphenol, octylphenol, nonylphenol, alkylphenol polyglycol ethers, tributylphenyl polyglycol ether, tristearylphenyl polyglycol ether, alkylaryl polyether alcohols, alcohol and fatty alcohol ethylene oxide condensates, ethoxylated castor oil, polyoxyethylene alkyl ethers, ethoxylated polyoxypropylene, lauryl alcohol polyglycol ether acetal, sorbitol esters, lignosulfite waste liquors, and methylcellulose. Examples of anti-freezing agents include glycerin, ethylene glycol, and propylene glycol. Suitable antifoaming agents include, for example, antifoaming agents based on silicon or magnesium stearate. Suitable preservatives include, for example, dichlorophen and enzylalkoholhemiformal. Suitable binders include, for example, block copolymers EO/PO surfactants but also polyvinylalcohols, polyvinylpyrrolidones, polyacrylates, polymethacrylates, polybutenes, polyisobutylenes, polystyrene, polyethyleneamines, polyethyleneamides, polyethyleneimines (LUPASOL, POLYMIN), polyethers, polyurethans, polyvinylacetate, tylose, and copolymers derived from these polymers. Suitable colorants or dyes are Rhodamin B, C.I. Pigment Red 112, C.I. Solvent Red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid violet 23, basic red 10, and basic red 108. An example of a suitable gelling agent is carrageen (SATIAGEL). Other additives that may be found in an herbicide formulation include other herbicides, adjuvants, detergents, spreading agents, sticking agents, stabilizing agents, or the like. Suitable adjuvants include, for example, a crop oil concentrate (COC), organo-modified siloxane (e.g., Break-Thru®), petroleum-based surfactant (e.g., DASH®), or methylated seed/vegetable oil (MSO, MVOC). In some embodiments, the herbicide is applied with an adjuvant in the formulation at 0.5-1% v/v.

Powders, materials for spreading, and dustable products can be prepared by mixing or concomitantly grinding the active substances with a solid carrier. Granules (e.g., coated granules, impregnated granules, and homogeneous granules) can be prepared by binding the active compounds to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers (e.g., ammonium sulfate, ammonium phosphate, ammonium nitrate), urea, and products of vegetable origin (e.g., cereal meal, tree bark meal, wood meal, nutshell meal, cellulose powders).

Other rice herbicides and rice seed/plant treatments can also be used on the rice described herein. For example, chemicals (pesticides, growth enhancers, fertilizers, drought tolerance sprays), biologics (biochemicals, microbial spores), and seed dressings may be used.

Methods for Producing Plants and Controlling Weeds:

This present disclosure further provides methods for producing rice plants. In some embodiments, these methods involve planting a plurality of rice seeds provided herein under conditions favorable for the growth of rice plants.

The plants of rice cultivar CLHA02 have increased resistance to AHAS-inhibiting herbicides, particularly imidazolinone herbicides. Accordingly, the present disclosure also provides methods for combating undesired vegetation or controlling weeds in the vicinity of a rice plant. In some embodiments, the methods involve contacting rice seeds provided herein with an AHAS-inhibiting herbicide. In other embodiments, the methods comprise applying the AHAS-inhibiting herbicide to the weeds and to the rice plant post-emergence. The AHAS-inhibiting herbicide may be selected from the group consisting of an imidazolinone herbicide, a sulfonylurea herbicide, a triazolopyrimidine herbicide, a pyrimidinyloxybenzoate herbicide, a sulfonylamino-carbonyltriazolinone herbicide, or a mixture thereof. However, in preferred embodiments, the AHAS-inhibiting herbicide is an imidazolinone herbicide or a mixture of two or more imidazolinone herbicides.

Rice seeds may be contacted with the herbicide using any application method known in the art. The term "contacting" signifies that the active ingredient of the herbicide is on the surface of the seed at the time of application, though a greater or lesser amount of the ingredient may penetrate into the seed, depending on the method of application. Suitable seed treatment techniques include, without limitation, seed dressing, seed coating, seed dusting, seed soaking, and seed pelleting. In some embodiments, the herbicide is applied to the seeds before sowing and/or after pregermination. "Pregermination" refers to a process in which seeds are sprouted in the absence of soil. Thus, the phrase "after pregermination" refers to the period of development after germination has occurred (i.e., after the root penetrates through the seed coat).

For post-emergent use, herbicides are generally applied at a stage up to 5-leaf, preferably the 2-to-4-leaf stage (e.g., 5-10 d post-emergence), with a second application 7-21 days (preferably 8-14 d) thereafter. In some embodiments, the herbicide applications are completed by the 25th day post-emergence, or before the boot stage or before completion of the boot stage, but, in any event, all herbicide treatments are completed at least 45 days before harvest. In some embodiments, the final application of the herbicide is followed by field flooding within two days for rice varieties grown with flood. Post-emergent herbicides may be applied, for example, using a type of sprayer, hand pump, or spreader.

For the methods of the present invention, the preferred amount or concentration of the herbicide is an "effective amount" or "effective concentration", i.e., an amount or concentration that is sufficient to kill or inhibit the growth of a similar wild-type rice plant, rice plant tissue, rice plant cell, or rice seed, but that does not kill or inhibit as severely the growth of the herbicide-resistant plants, plant tissues, plant cells, and seeds. Typically, the effective amount of an herbicide is an amount that is routinely used in agricultural production systems to kill weeds of interest. Such amounts are known to those of ordinary skill in the art. Herbicide application rates generally range from 0.1 g to 10 kg of the active ingredient per 100 kg of seed, preferably from 1 g to 5 kg per 100 kg of seed, in particular from 1 g to 2.5 kg per 100 kg of seed.

The phrase "control of undesired vegetation" refers to the killing of weeds and/or otherwise retarding or inhibiting the normal growth of the weeds. A "weed" is any plant that grows in locations where it is undesired. The weeds may include, for example, dicotyledonous and monocotyledonous weeds. Dicotyledonous weeds include, but are not limited to, weeds of the genera: *Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus,* and *Taraxacum*. Monocotyledonous weeds include, but are not limited to, weeds of the genera: *Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristyslis, Sagittaria, Eleocharis, Scirpus, Paspalum, Ischaemum, Sphenoclea, Dactyloctenium, Agrostis, Alopecurus,* and *Apera*. In addition, the weeds of the present invention can include crop plants that are growing in an undesired location. For example, a soybean plant that is in a field that predominantly comprises rice plants can be considered a weed if the soybean plant is undesired. Another example of a weed is red rice, which is the same species as cultivated rice.

This present invention also provides methods for producing a rice seed or plant by crossing a first parent rice plant with a second parent rice plant, wherein either the first or second parent rice plant is of the line CLHA02. In some embodiments, a breeding cross is made to introduce new genetics into the CLHA02 progeny (as opposed to a self or a sib cross, made to select among existing genetic alleles). In these embodiments, a population of hybrid rice plants will be produced that, on average, derive 50% of their alleles from cultivar CLHA02. The resulting first generation ($F_1$) hybrid rice seeds may be harvested and used to grow plants that express a subset of characteristics from CLHA02. Alternatively, a plant of this population may be selected and repeatedly selfed or sibbed with a rice cultivar resulting from successive filial generations. In other embodiments, both the first and second parent rice plants can come from the rice cultivar CLHA02. However, advantageously, the rice cultivar is used in crosses with other, different, rice cultivars to produce $F_1$ rice seeds and plants with superior characteristics. In some embodiments, rice cultivar CLHA02 is crossed with a second rice plant that is transgenic. Rice cultivar CLHA02 may also be crossed with other species, including those of the family Graminaceae, and especially of the genera *Zea, Tripsacum, Croix, Schlerachne, Polytoca, Chionachne,* and *Trilobachne,* of the tribe Maydeae. See the section below titled "Breeding Methods" for a detailed description of breeding techniques that may utilized with the present invention.

In some embodiments, a CLHA02 progeny plant is selected that has molecular markers, morphological characteristics, and/or physiological characteristics in common with CLHA02 (e.g., those listed in Table 1). Techniques such as restriction fragment length polymorphism (RFLP), random amplified polymorphic detection (RAPD), amplified fragment length polymorphism detection (AFLP), polymerase chain reaction (PCR), DNA sequencing, allele specific oligonucleotide (ASO) probes, and hybridization (e.g., to DNA microarrays or beads) may be utilized to identify progeny that share particular traits (e.g., the S653N trait) with CLHA02. Alternatively, the entire genome could be sequenced.

The present invention also provides methods for introducing a desired trait into rice cultivar CLHA02. This may be accomplished using traditional breeding methods, such as backcrossing. Here, rice cultivar CLHA02 is crossed with a second rice line expressing the desired trait and progeny with both the desired trait and characteristics of CLHA02 are selected and crossed. These steps are repeated until plants with both the desired trait and essentially all the physiological and morphological characteristics of CLHA02 have been produced.

Alternatively, the desired trait may be introduced by transforming the rice cultivar with a transgene. The transgene may confer at least one trait selected from the following: herbicide resistance; insect resistance; resistance to bacterial, fungal, or viral disease; modified fatty acid metabolism; modified carbohydrate metabolism; and male sterility. See the section below titled "Transformation Methods" for a detailed description of transformation techniques that may utilized with the present invention. The transgenic cultivar produced by these methods may be crossed with another cultivar to produce a new transgenic cultivar. Alternatively, the transgene incorporated by these methods could be moved into another cultivar using traditional backcrossing techniques.

Optionally, any of the disclosed methods may further comprise additional steps involving producing rice seed from the resulting rice plants and/or planting the rice seed.

The present invention encompasses all plants, or parts thereof, produced by the methods described herein, as well as the seeds produced by these plants. Further, any plants derived from rice cultivar CLHA02 or produced from a cross using cultivar CLHA02 are provided. This includes genetic variants, created either through traditional breeding methods or through transformation, as well as plants produced in a male-sterile form. Notably, this includes gene-converted plants developed by backcrossing. Any of the seeds, plants, or plant parts provided may be utilized for human food, livestock feed, and as a raw material in industry.

The present invention also encompasses progeny of rice cultivar CLHA02 comprising a combination of at least two CLHA02 traits selected from those listed in the Tables and Detailed Description, wherein the progeny rice plant is not significantly different from CLHA02 for said traits as determined at the 5% significance level when grown in the same environment. One of skill in the art knows how to compare a trait between two plant varieties to determine if there is a significant difference between them (Fehr and Walt, Principles of Cultivar Development, pp. 261-286 (1987)). Molecular markers or mean trait values may be used to identify a plant as progeny of CLHA02. Alternatively, progeny may be identified through their filial relationship with rice cultivar CLHA02 (e.g., as being within a certain number of breeding crosses of rice cultivar CLHA02). For example, progeny produced by the methods described herein may be within 1, 2, 3, 4, or 5 breeding crosses of rice cultivar CLHA02.

The disclosure also encompasses methods for preparing a commodity product, comprising processing a CLHA02 plant or plant part, seed, or progeny thereof to produce a product, such as food, feed, fuel, starch, meal, flour, germ meal, protein, oil, bran, fiber, paper, bedding, wax, phytochemicals, or polished, cooked, steamed, or parboiled grain.

Tissue Culture:

The present invention provides tissue cultures of regenerable cells or protoplasts produced from rice cultivar CLHA02. As is well known in the art, tissue culture of rice can be used for the in vitro regeneration of a rice plant. Thus, such cells and protoplasts may be used to produce plants having the physiological and morphological characteristics of rice cultivar CLHA02. The rice plants regenerated by these methods are also encompassed by the present invention.

As used herein, the term "tissue culture" describes a composition comprising isolated cells that are grown in culture. Exemplary tissues for culture include protoplasts, calli, plant clumps, and plant cells that can be grown in culture, or parts of plants, such as embryos, pollen, flowers, seeds, pods, leaves, stems, roots, root tips, and anthers. Culture of various rice tissues and regeneration of plants therefrom is well known in the art.

Breeding Methods:

The goal of rice breeding is to develop new, superior rice cultivars and hybrids. A superior cultivar is produced when a new combination of desirable traits is formed within a single plant cultivar. Desirable traits may include higher seed yield, resistance to diseases and insects, better stems and roots, tolerance to low temperatures, and better agronomic characteristics or grain quality.

Use of rice cultivar CLHA02 in any plant breeding method is encompassed by the present invention. In one embodiment, the method comprises crossing rice cultivar CLHA02 or its progeny, or a plant comprising all but 1, 2, 3, or more of the morphological and physiological characteristics of CLHA02 (e.g., as listed in Tables 1), with a different rice plant. In these methods, one or more offspring of the cross are subjected to one or more plant breeding techniques.

The choice of a breeding or selection method will depend on several factors, including the mode of plant reproduction, the heritability of the trait(s) being improved, and the type of cultivar used commercially (e.g., $F_1$ hybrid cultivar, pureline cultivar). The breeding methods used with the present invention may involve a single-seed descent procedure, in which one seed per plant is harvested and used to plant the next generation. Alternatively, the methods may utilize a multiple-seed procedure, in which one or more seeds harvested from each plant in a population is threshed together to form a bulk which is used to plant the next generation. Popular selection methods include pedigree selection, modified pedigree selection, mass selection, recurrent selection, backcrossing, mutation breeding. and/or genetic marker enhanced selection.

Pedigree selection is commonly used for the improvement of self-pollinating crops. Two parents are crossed to produce an $F_1$ population. An $F_2$ population is produced by selfing one or several $F_1$'s. Selection of the best individuals may begin in the $F_2$ population; then, beginning in the $F_3$ generation, the best individuals in the best families are selected. Replicative testing of families can begin in the $F_4$ generation to make selection of traits with low heritability more effective. At an advanced stage of inbreeding (e.g., $F_6$ or $F_7$), the best lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population, which is often subjected to additional cycles of selection.

Backcrossing is commonly used to transfer genes for highly heritable traits into a desirable homozygous cultivar or inbred line. The term "backcrossing" refers to the repeated crossing of hybrid progeny back to one of the parental plants, referred to as the recurrent parent. The plant that serves as the source of the transferred trait is called the donor parent. After the initial cross, individuals possessing the transferred trait are selected and repeatedly crossed to the recurrent parent. The resulting plant is expected to have the attributes of the recurrent parent along with the trait transferred from the donor parent.

Transformation Methods:

As is noted above, the present invention provides plants and seeds of rice cultivar CLHA02 in which additional traits have been transferred. While such traits may be selected for using traditional breeding methods, they may also be introduced as transgenes. "Transgenes" include both foreign genes and additional or modified versions of native genes. Plants can be genetically engineered to have a wide variety of traits of agronomic interest including, without limitation, male sterility, waxy starch, herbicide resistance, resistance for bacterial, fungal, or viral disease, insect resistance, male fertility, enhanced nutritional quality, industrial usage, yield stability, and yield enhancement. Many examples of genes that confer such traits have been described in the literature and are well known in the art. In certain preferred embodiments, the transgene confers resistance to an herbicide selected from the group consisting of glyphosate, sulfonylurea, imidazolinone, dicamba, glufosinate, phenoxy proprionic acid, L-phosphinothricin, cyclohexone, cyclohexanedione, triazine, 2,4-Dichlorophenoxyacetic acid, hydroxyphenyl-pyruvate dioxygenase (HPPD) inhibitors, and benzonitrile.

Transgenes are typically introduced in the form of an expression vector. As used herein, an "expression vector" is DNA comprising a gene operatively linked to a regulatory element (e.g., a promoter). The expression vector may contain one or more such gene/regulatory element combinations. The expression vector may also include additional sequences, such as a signal sequence or a tag, that modify the protein produced by the transgene. In some embodiments, the vector as a plasmid.

Expression vectors include at least one genetic marker operably linked to a regulatory element (e.g., a promoter) that allows transformed cells containing the vector to be recovered by selection. In some embodiments, negative selection (i.e., inhibiting growth of cells that do not contain the selectable marker gene) it utilized. Negative selection markers include, for example, genes that result in detoxification of a chemical agent (e.g., an antibiotic or an herbicide) and genes that result in insensitivity to an inhibitor. Exemplary negative selection genes include neomycin phosphotransferase II (nptII), hygromycin phosphotransferase, gentamycin acetyl transferase, streptomycin phosphotransferase, and aminoglycoside-3'-adenyl transferase. In other embodiments, positive selection (i.e., screening for the product encoded by a reporter gene) is utilized. Exemplary reporter genes include β-glucuronidase, β-galactosidase, luciferase, chloramphenicol acetyltransferase, and green fluorescent protein (GFP).

Transgene expression is typically driven by operably linking the transgene to a promoter within the expression vector. However, other regulatory elements may also be used to drive expression, either alone or in combination with a promoter. As used herein, a "promoter" is a region of DNA upstream of a transcription start site that is involved in recognition and binding of RNA polymerase for transcription initiation. Any class of promoter may be selected to drive the expression of a transgene. For example, the promoter may be "tissue-specific," "cell type-specific," "inducible," or "constitutive". Those of skill in the art know how to select a suitable promoter based the particular circumstances and genetic engineering goals.

Methods for producing transgenic plants are well known in the art. General descriptions of plant expression vectors, reporter genes, and transformation protocols can be found in Gruber, et al., "Vectors for Plant Transformation", in *Methods in Plant Molecular Biology & Biotechnology* in Glich, et al., (Eds. pp. 89-119, CRC Press, 1993). General methods of culturing plant tissues are provided for example by Maki et al., "Procedures for Introducing Foreign DNA into Plants" in *Methods in Plant Molecular Biology & Biotechnology*, Glich et al., (Eds. pp. 67-88 CRC Press, 1993); and by Phillips et al., "Cell-Tissue Culture and In-Vitro Manipulation" in *Corn & Corn Improvement,* 3rd Edition; Sprague et al., (Eds. pp. 345-387 American Society of Agronomy Inc., 1988). Methods of introducing expression vectors into plant tissue include direct gene transfer methods, such as microprojectile-mediated delivery, DNA injection, and electroporation, as well as the direct infection or co-cultivation of plant cells with *Agrobacterium tumefaciens*, described for example by Horsch et al., *Science,* 227:1229 (1985). Descriptions of *Agrobacterium* vector systems and methods for *Agrobacterium*-mediated gene transfer are provided by Gruber et al., supra.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

REFERENCES

Blanche, S B, X Sha, D L Harrell, D E Groth, K F Bearb, L M White, S D Linscombe. 2011. Registration of 'CL 151' Rice. J. Plant Registration 5:177-180.

Bollich, C N, C W Magill, A B Livore, H H Hung, B D Webb, M A Marchetti. 1993. Registration of 'Rosemont' rice. Crop Sci. 33:877.

Bollich, C N, B D Webb, M A Marchetti, J E Scott. 1980. Registration of Newrex rice 1 (Reg. No. 54). Crop Sci. 20:286-287.

Johnston, T H, B R Wells, M A Marchetti, F N Lee, S E Henry. 1979. Registration of Mars rice (Reg. No. 49). Crop Sci. 19:743-744.

Kuenzel, K A, T H Johnston, F N Lee, B R Wells, S E Henry, R H Dilday. 1986. Registration of 'Tebonnet' rice. Crop Sci. 25:1126-1127.

Reddy K R et al. 2021. Morpho-physiological characterization of diverse rice genotypes for seedling stage high- and low-temperature tolerance. Agronomy 11:112.

DEPOSIT INFORMATION

A deposit of rice cultivar CLHA02 has been made with the American Type Culture Collection (ATCC), 10801 University Boulevard, Manassas, Va. 20110. The date of deposit was Apr. 19, 2022. All restrictions will be irrevocably removed upon granting of a patent, and the deposit is intended to meet all of the requirements of 37 C.F.R. §§ 1.801-1.809. The ATCC Accession Number is PTA-127298. The deposit will be maintained in the depository for a period of thirty years, or five years after the last request, or for the enforceable life of the patent, whichever is longer, and will be replaced as necessary during that period. Breeder seed class of CLHA02 will also be maintained by the Delta Research and Extension Center, Mississippi Agricultural and Forestry Experiment Station, Mississippi State University in Stoneville, Mississippi.

What is claimed:

1. A rice seed of cultivar CLHA02, a representative sample of seed of said cultivar having been deposited under ATCC Accession No. PTA-127298.

2. The rice seed of claim 1, wherein said seed is treated with an acetohydroxyacid synthase (AHAS)-inhibiting herbicide.

3. The rice seed of claim 2, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and mixtures thereof.

4. The rice seed of claim 3, wherein said AHAS-inhibiting herbicide is an imidazolinone herbicide or a mixture of two or more imidazolinone herbicides.

5. The rice seed of claim 4, wherein the imidazolinone herbicide is selected from the group consisting of 2-(4-isopropyl-4-methyl-5-oxo-2-imidazolin-2-yl)-nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, mixtures of methyl-6-(4-isopropyl-4-methyl-5-oxo-2-imidazolin-2-yl)-m-toluate and methyl-2-(4-isopropyl-4-methyl-5-oxo-2-imidazolin-2-yl)-p-toluate, imazapyr, imazapic, imazethapyr, imazamox, imazamethabenz, and imazaquin herbicides, and mixtures thereof.

6. A rice plant, or a part thereof, produced by growing the seed of claim 1.

7. Pollen or an ovule of the plant of claim 6.

8. A method for producing rice plants, said method comprising planting a plurality of rice seeds as recited in claim 1 under conditions favorable for the growth of rice plants.

9. The method of claim 8, further comprising the step of producing rice seed from the resulting rice plants.

10. A rice seed produced by the method of claim 9.

11. A method for combating undesired vegetation or controlling weeds in the vicinity of a rice plant comprising contacting the rice seed of claim 1 with an AHAS-inhibiting herbicide before sowing and/or after pregermination.

12. The method of claim 11, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and mixtures thereof.

13. The method of claim 12, wherein said AHAS-inhibiting herbicide is an imidazolinone herbicide or a mixture of two or more imidazolinone herbicides.

14. A method for combating undesired vegetation or controlling weeds in the vicinity of a rice plant of cultivar CLHA02, the method comprising applying an effective amount of at least one AHAS-inhibiting herbicide to the weeds and to the rice plant, a representative sample of seed of said cultivar having been deposited under ATCC Accession No. PTA-127298.

15. The method of claim 14, wherein said AHAS-inhibiting herbicide is selected from the group consisting of imidazolinone herbicides, sulfonylurea herbicides, triazolopyrimidine herbicides, pyrimidinyloxybenzoate herbicides, sulfonylamino-carbonyltriazolinone herbicides, and combinations and mixtures thereof.

16. The method of claim 15, wherein said AHAS-inhibiting herbicide is an imidazolinone herbicide or a mixture of two or more imidazolinone herbicides.

17. The method of claim 16, wherein said imidazolinone herbicide is selected from the group consisting of 2-(4-isopropyl-4-methyl-5-oxo-2-imidazolin-2-yl)-nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, mixtures of methyl-6-(4-isopropyl-4-methyl-5-oxo-2-imidazolin-2-yl)-m-toluate and methyl-2-(4-isopropyl-4-methyl-5-oxo-2-imidazolin-2-yl)-p-toluate, imazapyr, imazapic, imazethapyr, imazamox, imazamethabenz, and imazaquin herbicides and mixtures thereof.

18. A tissue culture of regenerable cells or protoplasts produced from the rice plant of claim 6.

19. The tissue culture of claim 18, wherein said cells or protoplasts are produced from a tissue selected from the group consisting of embryos, meristematic cells, pollen, leaves, anthers, roots, root tips, pistils, anthers, cotyledon, hypocotyl, panicles, flowers, seeds, and stems.

20. A rice plant regenerated from the tissue culture of claim 18, wherein said rice plant has all of the morphological and physiological characteristics of cultivar CLHA02.

21. A method for producing an herbicide-resistant rice plant, the method comprising crossing a first parent rice plant with a second parent rice plant, wherein the first parent rice plant is the rice plant of claim 6.

22. The method of claim 21, wherein the second parent rice plant is not resistant to an herbicide.

23. The method of claim 21, wherein the first or second parent plant comprises a second trait other than the AHASL-S653 (At) N trait present in CLHA02.

24. The method of claim 21, further comprising selecting for a progeny rice plant that is resistant to at least one AHAS-inhibiting herbicide.

25. The method of claim 21, wherein said AHAS-inhibiting herbicide is an imidazolinone herbicide or a mixture of two or more imidazolinone herbicides.

26. An F1 herbicide-resistant rice plant produced by the method of claim 21.

27. The method of claim 21, further comprising the step of producing rice seed from the resulting rice plants.

28. The method of claim 21, wherein the second parent rice plant is transgenic.

29. A method comprising transforming the rice plant of claim 6 or cell thereof with a transgene, wherein the transgene confers at least one trait selected from the group consisting of herbicide resistance; insect resistance; resistance to bacterial, fungal, or viral disease; modified fatty acid metabolism; modified carbohydrate metabolism; and male sterility.

30. A rice plant or part thereof, or rice seed, produced by the method of claim 29.

31. A method of introducing a desired trait into rice cultivar CLHA02, said method comprising the steps of:
(a) crossing plants as recited in claim 6 with plants of another rice line expressing the desired trait, to produce progeny plants;
(b) selecting progeny plants that express the desired trait, to produce selected progeny plants;

(c) crossing the selected progeny plants with plants of rice cultivar CLHA02 to produce new progeny plants;
(d) selecting new progeny plants that express both the desired trait and some or all of the physiological and morphological characteristics of rice cultivar CLHA02, to produce new selected progeny plants; and
(e) repeating steps (c) and (d) three or more times in succession, to produce selected higher generation backcross progeny plants that express the desired trait.

32. The method of claim 31, wherein the desired trait is selected from the group consisting of herbicide resistance traits; insect resistance traits; traits of resistance to bacterial, fungal, or viral disease; modified fatty acid metabolism traits; modified carbohydrate metabolism traits; and male sterility traits.

33. The method of claim 32, wherein said AHAS-inhibiting herbicide is selected from the group consisting of imidazolinone herbicides, sulfonylurea herbicides, triazolopyrimidine herbicides; pyrimidinyloxybenzoate herbicides, sulfonylamino-carbonyltriazolinone herbicides, and combinations and mixtures thereof.

34. The method of claim 33, further comprising the step of planting a plurality of rice seed produced by selecting higher generation backcross progeny plants under conditions favorable for the growth of rice plants and optionally comprising the step of producing rice seed from the resulting rice plants.

35. A rice plant of cultivar CLHA02, a representative sample of seed of said cultivar having been deposited under ATCC Accession No. PTA-127298.

36. A method for preparing a commodity product, the method comprising processing a CLHA02 plant or plant part, seed, or progeny thereof of claim 35 to produce a product selected from the group consisting of food, feed, fuel, starch, meal, flour, germ meal, protein, oil, bran, fiber, paper, bedding, wax, phytochemicals, and polished, cooked, steamed, or parboiled grain.

37. A method for developing a rice plant in a breeding program, said method comprising applying plant breeding techniques comprising recurrent selection, backcrossing, mass selection, mutation breeding, genetic marker enhanced selection, or genetic transformation to the plant of claim 1 or part thereof, wherein said plant breeding techniques result in a development of a rice plant.

* * * * *